(12) United States Patent
Osawa et al.

(10) Patent No.: US 9,968,682 B2
(45) Date of Patent: *May 15, 2018

(54) POLYPEPTIDE HYDROGEL AND METHOD FOR PRODUCING SAME

(71) Applicant: SPIBER INC., Tsuruoka-shi, Yamagata (JP)

(72) Inventors: Toshiaki Osawa, Tsuruoka (JP); Keisuke Morita, Tsuruoka (JP)

(73) Assignee: SPIBER INC., Yamagata (JP)

( * ) Notice: Subject to any disclaimer, the term of this patent is extended or adjusted under 35 U.S.C. 154(b) by 36 days.

This patent is subject to a terminal disclaimer.

(21) Appl. No.: 14/764,455

(22) PCT Filed: Apr. 18, 2014

(86) PCT No.: PCT/JP2014/061041
§ 371 (c)(1),
(2) Date: Jul. 29, 2015

(87) PCT Pub. No.: WO2014/175177
PCT Pub. Date: Oct. 30, 2014

(65) Prior Publication Data
US 2015/0374833 A1    Dec. 31, 2015

(30) Foreign Application Priority Data

Apr. 25, 2013  (JP) ................. 2013-092847

(51) Int. Cl.
| A61K 9/08 | (2006.01) |
|---|---|
| A61K 38/17 | (2006.01) |
| A61L 27/22 | (2006.01) |
| A61L 27/52 | (2006.01) |
| A61K 47/42 | (2017.01) |
| A61L 26/00 | (2006.01) |
| A61L 31/14 | (2006.01) |
| A61K 9/00 | (2006.01) |
| C07K 14/435 | (2006.01) |
| A61L 27/36 | (2006.01) |
| A61L 27/60 | (2006.01) |

(52) U.S. Cl.
CPC ............ *A61K 47/42* (2013.01); *A61K 9/0087* (2013.01); *A61K 38/1767* (2013.01); *A61L 26/008* (2013.01); *A61L 27/227* (2013.01); *A61L 27/3604* (2013.01); *A61L 27/3687* (2013.01); *A61L 27/52* (2013.01); *A61L 27/60* (2013.01); *A61L 31/145* (2013.01); *C07K 14/43518* (2013.01); *A61L 2430/06* (2013.01)

(58) Field of Classification Search
CPC .... A61K 9/0087; A61K 9/08; A61K 38/1767; A61L 26/008; A61L 27/52; A61L 31/145; A61L 2430/06; C07K 14/43518
See application file for complete search history.

(56) References Cited

U.S. PATENT DOCUMENTS

| 4,448,750 A | 5/1984 | Fuesting |
|---|---|---|
| 5,728,810 A | 3/1998 | Lewis et al. |
| 5,853,764 A | 12/1998 | Tsubouchi |
| 5,989,894 A | 11/1999 | Lewis et al. |
| 6,620,917 B1 | 9/2003 | Mello et al. |
| 6,919,075 B1 | 7/2005 | Solomon et al. |
| 8,153,591 B2 | 4/2012 | Masters |
| 2002/0081286 A1 | 6/2002 | Marchionni |
| 2005/0158821 A1 | 7/2005 | Mello et al. |
| 2006/0273279 A1 | 12/2006 | Kaplan et al. |
| 2007/0187862 A1 | 8/2007 | Kaplan et al. |
| 2007/0214520 A1 | 9/2007 | Scheibel et al. |
| 2008/0141792 A1 | 6/2008 | Li et al. |
| 2009/0123967 A1 | 5/2009 | Scheibel |
| 2010/0278883 A1 | 11/2010 | Liebmann et al. |
| 2010/0317588 A1 | 12/2010 | Shoseyov et al. |
| 2011/0136669 A1 | 6/2011 | Liebmann et al. |
| 2011/0287009 A1 | 11/2011 | Scheer et al. |
| 2012/0148639 A1 | 6/2012 | Tamada et al. |
| 2013/0109762 A1 | 5/2013 | Lammel et al. |
| 2013/0225793 A1 | 8/2013 | Shoseyov et al. |
| 2014/0011871 A1 | 1/2014 | Rockhill |
| 2014/0086874 A1 | 3/2014 | Nazhat |
| 2014/0245923 A1 | 9/2014 | Sugahara et al. |
| 2014/0256641 A1 | 9/2014 | Shoseyov et al. |
| 2015/0094452 A1 | 4/2015 | Shoseyov et al. |
| 2015/0329587 A1 | 11/2015 | Osawa |
| 2015/0344542 A1 | 12/2015 | Osawa |
| 2015/0361144 A1 | 12/2015 | Osawa |
| 2015/0376247 A1 | 12/2015 | Osawa |

FOREIGN PATENT DOCUMENTS

| CN | 1560136 | 1/2005 |
|---|---|---|
| CN | 102176904 | 9/2011 |

(Continued)

OTHER PUBLICATIONS

Schacht et al.: "Controlled Hydrogel Formation of a Recombinant Spider Silk Protein"; Biomacromolecules, (2011), 12(7), pp. 2488-2495.

(Continued)

*Primary Examiner* — Jeffrey E. Russel
(74) *Attorney, Agent, or Firm* — Hamre, Schumann, Mueller & Larson, P.C.

(57) ABSTRACT

A polypeptide hydrogel of the present invention is a hydrogel of a polypeptide derived from spider silk proteins, and has a moisture content of 85.0 to 99.9 mass % based on 100 mass % of the polypeptide hydrogel. A method for producing the hydrogel includes: a solution production step in which a polypeptide derived from spider silk proteins is dissolved in at least one dissolving solvent selected from the group consisting of: (A) dimethyl sulfoxide; (B) dimethyl sulfoxide with an inorganic salt; and (C) N, N-dimethylformamide with an inorganic salt, so as to obtain a solution of the polypeptide; and a substitution step in which the solution produced in the solution production step is substituted with a water-soluble solvent. Thus, the present invention provides a polypeptide hydrogel having excellent water retentivity and a polypeptide hydrogel suitable for application to a living body.

5 Claims, 1 Drawing Sheet

(56) References Cited

FOREIGN PATENT DOCUMENTS

| CN | 102344686 | 2/2012 |
|---|---|---|
| EP | 0 452 925 | 4/1991 |
| EP | 2 599 790 | 6/2013 |
| EP | 2 990 413 | 3/2016 |
| JP | 1-118544 | 5/1989 |
| JP | 2-240165 | 9/1990 |
| JP | 6-98771 | 4/1994 |
| JP | 11-217506 | 8/1999 |
| JP | 2003-509020 | 3/2003 |
| JP | 2004-503204 | 2/2004 |
| JP | 2007-515391 | 6/2007 |
| JP | 2008-506409 | 3/2008 |
| JP | 2009-505668 | 2/2009 |
| JP | 2011-504374 | 2/2011 |
| JP | 2012-082241 | 4/2012 |
| JP | 2012-082244 | 4/2012 |
| JP | 2 774 934 | 9/2014 |
| JP | 2 940 033 | 11/2015 |
| RU | 2478706 | 4/2013 |
| WO | 01/18169 | 3/2001 |
| WO | 01/53333 | 7/2001 |
| WO | 2002-186847 | 7/2002 |
| WO | 02/096931 | 12/2002 |
| WO | 2004/062697 | 7/2004 |
| WO | 2005/124011 | 12/2005 |
| WO | 2006-249115 | 9/2006 |
| WO | 2007/082936 | 7/2007 |
| WO | 2007/100524 | 9/2007 |
| WO | 2009/069123 | 6/2009 |
| WO | 2010/015419 | 2/2010 |
| WO | 2011/021712 | 2/2011 |
| WO | 2011/063990 | 6/2011 |
| WO | 2011/133886 | 10/2011 |
| WO | 2012/074588 | 6/2012 |

OTHER PUBLICATIONS

International Search Report, dated Jul. 22, 2014; PCT/JP2014/061041.
Rabotyagova, et al., "Self-Assembly of Genetically Engineered Spider Silk Block Copolymers", Biomacromolecules, vol. 10, No. 2, Jan. 2009, pp. 229-326.
Fu, et al., "Animal silks: their structures, properties and artificial production", Chemical Communications, No. 43, Jan. 2009, pp. 6515-6529.
Um, et al., "Wet spinning of silk polymer I. Effect of coagulation conditions on the morphological feature of filament", International Journal of Biological Macromolecules, vol. 34, No. 1-2, Apr. 2004, pp. 89-105.
Extended European Search Report issued in corresponding European Patent Application No. 14787823.5, dated Oct. 10, 2016, 12 pages.
Extended European Search Report issued in corresponding European Patent Application No. 14787816.9, dated Sep. 7, 2016, 8 pages.
Office Action issued in corresponding Chinese Patent Application No. 201480005729.6, dated Nov. 14, 2016, 14 pages with a machine translation.
Diao, et al., "Solubility and Electrospun Regenerated Fiber of Two Different Kinds of Spider Silk", Journal of Materials Science & Engineering, vol. 26, No. 6, Dec. 2008. pp. 918-922—English Abstract.
Extended European Search issued for corresponding European Patent Application No. 14788691.5, dated Dec. 6, 2016, 8 pages.
U.S. Appl. No. 14/655,017, filed Jun. 23, 2015, US 2015/0329587.
U.S. Appl. No. 14/655,027, filed Jun. 23, 2015, US 2015/0344542.
U.S. Appl. No. 14/764,463, filed Jul. 29, 2015, US 2015/0361144.
U.S. Appl. No. 14/764,472, filed Jul. 29, 2015, US 2015/0376247.
Rammensee et al.: "Rheological characterization of hydrogels formed by recombinantly produced spider silk"; Appl. Phys. A Matr Sci. Process, 2006, vol. 82, No. 2, pp. 261-264.
Vepari C. et al.: "Silk as a biomaterial"; Polym. Sci., 2007, vol. 32, No. 8-9, pp. 991-1007.
Japanese Office Action, dated Jul. 23, 2015; Japanese Patent Application No. 2015-513727 with English translation (10 pages).
Application of co-pending U.S. Appl. No. 14/764,463, filed Jul. 29, 2015.
Application of co-pending U.S. Appl. No. 14/764,472, filed Jul. 29, 2015.
Hofer et al.: "Recombinant spider silk particles for controlled delivery of protein drugs", Biomaterials, (2012), vol. 33, pp. 1554-1562.
U.S. Appl. No. 14/764,463, filed Jul. 29, 2015.
U.S. Appl. No. 14/764,472, filed Jul. 29, 2015.
Kyte, et al., "A Simple Method for Displaying the Hydropathic Character of a Protein", J. Mol. Biol., vol. 157, 1982, pp. 105-132.
Elvin, et al., "Synthesis and Properties of crosslinked recombinant pro-resilin", Nature, vol. 437, Oct. 13, 2005, pp. 999-1002.
Extended European Search Report issued in corresponding European Patent Application, dated Sep. 13, 2016, 9 pages.
Nic, et al., "dipolar aprotic solvent" In: "IUPAC Compendium of Chemical Terminology" IUPAC, The Research Triangle Park, NC, doi: 10.1351/goldbook.D01751, Feb. 24, 2014, 1 page.
Chang, et al., "Protein Separation and Purification in Neat Dimethyl Sulfoxide", Biochemical and Biophysical Research Communications, vol. 176, No. 3, May 15, 1991, pp. 1462-1468.
The solvent substitution p. Of the chemistry innovation web page, available Feb. 2010 http://www.chemistryinnovation.co.uk/roadmap/sustainable/roadmap.asp?id=84.
Wang, et al., "Cell lysis with dimethyl sulphoxide produces stable homogeneous solutions in the dichlorofluorescein oxidative stress assay.", Free Radical Res. (2008) 42(5) p. 435-441.
Reynolds, et al., Method of Determining Nanoparticle Core Weight, Anal. Chem. 2005, 77(3), 814-817.
Tamada, "New Process to Form a Silk Fibroin Porous 3-D Structure", Biomacromolecules, 2005, 6(6): 3100-3106.
Colonne, et al.,"Hijacking Host Cell Highways: Manipulation of the Host Actin Cytoskeleton by Obligate Intracellular Bacterial Pathogens", Frontier Cell. Infect. Microbiol., Sep. 2016, vol. 6, pp. 1-8.
Ramya, et al., "Expression and Solubilization of Insect Cell-Based Rabies Virus Blycoprotein and Assessment of Its Immunogenicity and Protective Efficacy in Mice", Clin. Vaccine Immunol., Oct. 2011, vol. 18, No. 10, pp. 1673-1679.
Becker, "Putative Antigenic Domains in Glycoprotein G of Rabies Virus: Is the RGK Sequence Involved in Virus Adsorption to Cellular Receptors?", Virus Genes, vol. 3, No. 3, pp. 277-284 (1990).

POLYPEPTIDE HYDROGEL AND METHOD FOR PRODUCING SAME

TECHNICAL FIELD

The present invention relates to a polypeptide hydrogel made from a polypeptide derived from spider silk proteins, and a method for producing the same.

BACKGROUND ART

A polypeptide hydrogel is used as a biomaterial for artificial cartilage, etc. Patent Document 1 proposes a hydrogel obtained by dissolving silk fibroin in a hygroscopic polymer such as polyethylene glycol. Patent Document 2 discloses a photocrosslinked gel made from spider silk.

PRIOR ART DOCUMENTS

Patent Documents

Patent Document 1: JP 2007-515391 A
Patent Document 2: JP 2008-506409 A

DISCLOSURE OF INVENTION

Problem to be Solved by the Invention

However, an urea aqueous solution, which is a conventionally proposed solvent, does not have a sufficient power to dissolve spider silk proteins, and a guanidine aqueous solution, hexafluoroisopropanol (HFIP), and the like are expensive and have a problem in application to a human body if they remain in a product. Further, it is hard to say that the water retentivity of conventional silk fibroin hydrogels is sufficiently high.

To solve the above conventional problems, the present invention provides a polypeptide hydrogel having excellent water retentivity and a polypeptide hydrogel suitable for application to a living body, and a method for producing the same.

Means for Solving Problem

A polypeptide hydrogel of the present invention is a hydrogel of a polypeptide derived from spider silk proteins, and has a moisture content of 85.0 to 99.9 mass % based on 100 mass % of the polypeptide hydrogel.

A method for producing a polypeptide hydrogel of the present invention includes: a solution production step in which a polypeptide derived from spider silk proteins is dissolved in at least one dissolving solvent selected from the group consisting of: (A) dimethyl sulfoxide; (B) dimethyl sulfoxide with an inorganic salt; and (C) N,N-dimethylformamide with an inorganic salt, so as to obtain a solution of the polypeptide; and a substitution step in which the solution of the polypeptide produced in the solution production step is substituted with a water-soluble solvent. Incidentally, "a polypeptide is dissolved in a dissolving solvent" used herein includes both of a state in which a polypeptide is completely dissolved in a dissolving solvent and a state in which polypeptide microparticles are dispersed in a dissolving solvent and thus are substantially dissolved in the dissolving solvent. Hereinafter, the expression shall have the same meaning as described above.

Effect of the Invention

A polypeptide hydrogel of the present invention has a moisture content of 85.0 to 99.9 mass % based on 100 mass % of the polypeptide hydrogel, and thus exhibits higher water retentivity. Because of this, the polypeptide hydrogel of the present invention can advantageously be applied to artificial cartilage, artificial skin, a wound-healing agent, a medicament-encapsulated carrier in a drug delivery system, etc. Further, by using a specific solvent in the production of the polypeptide solution and substituting the solvent with a water-soluble solvent, the present invention can provide a polypeptide hydrogel in which the amount of the remaining solvent is little or the amount of the remaining solution is sufficiently low. Additionally, the solvents used in the present invention are those that have been used in the production of acrylic fibers and polyimid resin, and they are low cost.

DESCRIPTION OF THE INVENTION

A polypeptide derived from spider silk proteins is used as the protein of the present invention. The polypeptide derived from spider silk proteins is not limited particularly as long as it is derived from or similar to natural type spider silk proteins. Examples of the polypeptide derived from spider silk proteins include variants, analogs, derivatives, and the like of natural type spider silk proteins. In terms of excellent tenacity, the recombinant spider silk protein preferably is a recombinant spider silk protein derived from major dragline silk proteins produced in major ampullate glands of spiders. Examples of the major dragline silk proteins include major ampullate spidroins MaSp1 and MaSp2 derived from Nephila clavipes, and ADF3 and ADF4 derived from Araneus diadematus, etc.

The recombinant spider silk protein may be a recombinant spider silk protein derived from minor dragline silk produced in minor ampullate glands of spiders. Examples of the minor dragline silk proteins include minor ampullate spidroins MiSp1 and MiSp2 derived from Nephila clavipes.

Other than these, the recombinant spider silk protein may be a recombinant spider silk protein derived from flagelliform silk proteins produced in flagelliform glands of spiders. Examples of the flagelliform silk proteins include flagelliform silk proteins derived from Nephila clavipes, etc.

Examples of the polypeptide derived from major dragline silk proteins include a polypeptide containing two or more units of an amino acid sequence represented by the formula 1: REP1-REP2 (1), preferably a polypeptide containing four or more units thereof, and more preferably a polypeptide containing six or more units thereof. In the polypeptide derived from major dragline silk proteins, units of the amino acid sequence represented by the formula (1): REP1-REP2 (1) may be the same or different from each other. In the formula (1), the REP1 represents polyalanine.

In the REP1, the number of alanine residues arranged in succession is preferably 2 or more, more preferably 3 or more, further preferably 4 or more, and particularly preferably 5 or more. Further, in the REP1, the number of alanine residues arranged in succession is preferably 20 or less, more preferably 16 or less, further preferably 14 or less, and particularly preferably 12 or less. In the formula (1), the REP2 is an amino acid sequence composed of 10 to 200 amino acid residues. The total number of glycine, serine, glutamine, proline, and alanine residues contained in the amino acid sequence is 40% or more, preferably 50% or more, and more preferably 60% or more with respect to the total number of amino acid residues contained therein.

In the major dragline silk, the REP1 corresponds to a crystal region in a fiber where a crystal β sheet is formed, and the REP2 corresponds to an amorphous region in a fiber where most of the parts lack regular structures and that has more flexibility. Further, the [REP1-REP2] corresponds to a repetitious region (repetitive sequence) composed of the crystal region and the amorphous region, which is a characteristic sequence of dragline silk proteins.

An example of the polypeptide containing two or more units of the amino acid sequence represented by the formula 1: REP1-REP2 (1) is a recombinant spider silk protein derived from ADF3 having an amino acid sequence represented by any of SEQ ID NO: 1, SEQ ID NO: 2, SEQ ID NO: 3 and SEQ ID NO: 4. The amino acid sequence represented by SEQ ID NO: 1 is an amino acid sequence from the 1st residue to the 631st residue of an amino acid sequence that is obtained by adding an amino acid sequence (SEQ ID NO: 5) composed of a start codon, an His 10-tag and an HRV3C Protease (Human rhinovirus 3C Protease) recognition site to the N-terminal of a partial amino acid sequence of ADF3 obtained from the NCBI database (NCBI Genebank Accession No.: AAC47010, GI: 1263287). The amino acid sequence represented by SEQ ID NO: 2 is an amino acid sequence obtained by the following mutation: in an amino acid sequence of ADF3 (NCBI Genebank Accession No.: AAC47010, GI: 1263287) to the N-terminal of which has been added the amino acid sequence (SEQ ID NO: 5) composed of a start codon, an His 10-tag and an HRV3C Protease (Human rhinovirus 3C Protease) recognition site, 1st to 13th repetitive regions are about doubled and the translation ends at the 1154th amino acid residue. The amino acid sequence represented by SEQ ID NO: 3 is an amino acid sequence obtained by adding the amino acid sequence (SEQ ID NO: 5) composed of a start codon, an His 10-tag and an HRV3C Protease (Human rhinovirus 3C Protease) recognition site, to the N-terminal of a partial amino acid sequence of ADF3 (NCBI Genebank Accession No.: AAC47010, GI: 1263287) obtained from the NCBI database. The amino acid sequence represented by SEQ ID NO: 4 is an amino acid sequence obtained as follows: in an amino acid sequence of ADF3 (NCBI Genebank Accession No.: AAC47010, GI: 1263287) to the N-terminal of which has been added the amino acid sequence (SEQ ID NO: 5) composed of a start codon, an His 10-tag and an HRV3C Protease (Human rhinovirus 3C Protease) recognition site, 1st to 13th repetitive regions are about doubled. Further, the polypeptide containing two or more units of the amino acid sequence represented by the formula 1: REP1-REP2 (1) may be a polypeptide that is composed of an amino acid sequence represented by any of SEQ ID NO: 1, SEQ ID NO: 2, SEQ ID NO: 3 and SEQ ID NO: 4 in which one or a plurality of amino acids have been substituted, deleted, inserted and/or added and that has repetitious regions composed of crystal regions and amorphous regions.

In the present invention, "one or a plurality of" refers to 1 to 40, 1 to 35, 1 to 30, 1 to 25, 1 to 20, 1 to 15, 1 to 10, or 1 or a few, for example. Further, in the present invention, "one or a few" refers to 1 to 9, 1 to 8, 1 to 7, 1 to 6, 1 to 5, 1 to 4, 1 to 3, 1 to 2, or 1.

An example of the recombinant spider silk protein derived from minor dragline silk proteins is a polypeptide containing an amino acid sequence represented by the formula 2: REP3 (2). In the formula 2, the REP 3 indicates an amino acid sequence composed of (Gly-Gly-Z)m(Gly-Ala)l(A)r (SEQ ID NO.: 7), where Z indicates any one of amino acids, particularly, it preferably is an amino acid selected from the group consisting of Ala, Tyr and Gln. Further, preferably, m is 1 to 4, 1 is 0 to 4, and r is 1 to 6.

Among spider silks, the minor dragline silk is wound spirally from the center of a spider net, and used as a reinforcement of the net and a yarn to wrap a captured prey. The minor dragline silk is inferior to the major dragline silk in tensile strength, but is known to have high stretchability. The reason for this is considered to be as follows: in the minor dragline silk, since many crystal regions are formed of regions where glycine and alanine are arranged alternately in succession, hydrogen bonds in the crystal regions weaken easily as compared with the major dragline silk whose crystal regions are formed only of alanine.

Examples of the recombinant spider silk protein derived from flagelliform silk proteins include a polypeptide containing an amino acid sequence represented by the formula 3: REP4 (3). In the formula 3, the REP 4 indicates an amino acid sequence composed of (Gly-Pro-Gly-Gly-X (SEQ ID NO.: 8))n, where X indicates any one of amino acids, in particular, it preferably is an amino acid selected from the group consisting of Ala, Ser, Tyr and Val. Further, n indicates a number of 4 or larger, preferably 10 or larger, and more preferably 20 or larger.

Among spider silks, the flagelliform silk does not have crystal regions but has repetitious regions composed of amorphous regions, which is a major characteristic of the flagelliform silk. It is considered that since the major dragline silk and the like have repetitious regions composed of crystal regions and amorphous regions, they have both of high strength and stretchability. Meanwhile, regarding the flagelliform silk, the strength is inferior to that of the major dragline silk but the stretchability is high. The reason for this is considered to be that the flagelliform silk is composed mostly of amorphous regions.

The polypeptide can be produced using a host that has been transformed by an expression vector containing a gene encoding a polypeptide. A method for producing a gene is not limited particularly, and it may be produced by amplifying a gene encoding a natural type spider silk protein from a cell containing the desired gene of spider by a polymerase chain reaction (PCR), etc., and cloning it, or may be synthesized chemically. A method for chemically synthesizing a gene also is not limited particularly, and it can be synthesized as follows, for example: based on information of amino acid sequences of natural type spider silk proteins obtained from the NCBI web database, oligonucleotides that have been synthesized automatically with AKTA oligopilot plus 10/100 (GE Healthcare Japan Corporation) are linked by PCR, etc. At this time, in order to facilitate purification and observation of protein, a gene may be synthesized that encodes a protein composed of an amino acid sequence in which an amino acid sequence composed of a start codon and an His 10-tag has been added to the N-terminal of the amino acid sequence. Examples of the expression vector include a plasmid, a phage, a virus, and the like that can express protein based on a DNA sequence. The plasmid-type expression vector is not limited particularly as long as it allows a target gene to be expressed in a host cell and it can amplify itself. For example, in the case of using *Escherichia coli* Rosetta (DE3) as a host, a pET22b(+) plasmid vector, a pCold plasmid vector, and the like can be used. Among these, in terms of productivity of protein, the use of the pET22b(+) plasmid vector is preferred. Examples of the host include animal cells, plant cells, microbes, etc.

Further, a preferable example of the polypeptide is a polypeptide that aggregates easily (easy aggregation property) when the solution produced in the solution production step is substituted with a water-soluble solvent. Thus, regardless of the concentration of the polypeptide in the solution, a gel can be produced easy. Incidentally, even if a polypeptide does not have such an easy aggregation property, for example, by increasing the concentration of the polypeptide in the solution produced in the solution production step, the polypeptide aggregates when the solution is substituted with a water-soluble solvent. Thus, a gel can be produced easily. The polypeptide also may aggregate by lowering the temperature from a high-temperature state to a low-temperature state. In other words, a polypeptide hydrogel is produced by substituting the solution produced in the solution production step with a water-soluble solvent so as to aggregate polypeptide. Further, in the production of the polypeptide hydrogel, a polypeptide that aggregates upon contact with a water-soluble solvent and thus is capable of forming a gel is used.

The gel of the present invention has a moisture content of 85.0 to 99.9 mass %, preferably 90.0 to 99.7 mass %, and more preferably 92.0 to 99.5 mass % based on 100 mass % of the polypeptide hydrogel. The moisture herein refers to liquid water. When containing the moisture in the above range, the gel of the present invention can be applied as, e.g., artificial cartilage and artificial skin of a living body, a wound-healing agent, a medicament-encapsulated carrier in a drug delivery system, etc.

The gel of the present invention can be produced by: a solution production step in which a polypeptide derived from spider silk proteins is dissolved in at least one dissolving solvent selected from the group consisting of (A) dimethyl sulfoxide; (B) dimethyl sulfoxide with an inorganic salt; and (C) N,N-dimethylformamide with an inorganic salt, so as to obtain a solution of the polypeptide; and a substitution step in which the solution of the polypeptide produced in the solution production step is substituted with a water-soluble solvent. The gel can be formed into a predetermined shape by performing a molding step in which the solution is poured into a mold between the solution production step and the step of substituting the dissolving solvent with a water-soluble solvent, or by cutting the gel after the step of substituting the dissolving solvent with a water-soluble solvent. At least one selected from the group consisting of dimethyl sulfoxide and N,N-dimethylformamide may be present inside the obtained polypeptide hydrogel. The amount of the dissolving solvent present therein is not limited particularly, and it is an amount that remains therein unintentionally after the solution produced in the solution production step is substituted with the water-soluble solvent.

In addition to the substances indicated in (A)-(C) above, the dissolving solvent may contain alcohol and/or water. The dissolving solvent is a polar solvent, and tends to absorb moisture in air. Therefore, in some cases, commercial solvents contain several % of water. The dissolving solvent may contain this amount of water and/or alcohol. Incidentally, the substances functioning as the dissolving solvent are those indicated in (A)-(C) above.

The water-soluble solvent refers to a solvent containing water. Examples of the water-soluble solvent include water, a water-soluble buffer solution, and saline. In terms of high compatibility with the human body, preferably, the water-soluble solvent is water. Although the water is not limited particularly, it may be pure water, distilled water, ultrapure water, etc.

The viscosity of the solution after the solution production step is preferably 5 to 80 cP (centipoises), and more preferably 10 to 50 cP. Within the above range, favorable handleability and convenience will be obtained.

In the present invention, a solvent containing DMSO and/or DMF (polar solvent) is used as the solvent. DMSO has a melting point of 18.4° C. and a boiling point of 189° C. DMF has a melting point of −61° C. and a boiling point of 153° C. DMSO and DMF have much higher boiling points than hexafluoroisopropanol (HFIP) and hexafluoroacetone (HFAc) having boiling points of 59° C. and −26.5° C., respectively, which have been used in conventional methods, and hence DMSO and DMF have favorable dissolubility. Further, in view of the fact that DMSO and DMF have been used also in general industrial fields for acrylic fiber polymerization, acrylic fiber spinning solutions, and solvents for polyimide polymerization, they are low-cost substances with proven safety.

Addition of an inorganic salt to DMSO or DMF further increases the solubility of a solute. The inorganic salt is at least one selected from alkali metal halides (e.g., LiCl, LiBr, etc.), alkaline-earth metal halides (e.g., $CaCl_2$), alkaline-earth metal nitrate (e.g., $Ca(NO_3)_2$, etc.), and sodium thiocyanate (e.g., NaSCN, etc.). When the dissolved components are assumed to be 100 mass %, the percentage of the inorganic salt preferably ranges from 0.1 to 20 mass %.

The polypeptide hydrogel is produced by substituting the solvent with the water-soluble solvent. Further, preferably, the step of substituting the solvent with the water-soluble solvent is performed in the following manner: the solution of the polypeptide obtained by dissolving the polypeptide in the solvent is placed in a dialysis membrane, the dialysis membrane is immersed in a water-soluble solvent, and the water-soluble solvent is renewed at least one time. Specifically, preferably, the step of substituting the solvent with the water-soluble solvent is performed by placing the solution after the solution production step in a dialysis membrane, leaving it to stand for 3 hours in a water-soluble solvent in an amount 100 times or more the amount of the solution (one batch), and renewing the water-soluble solvent three or more times in total. Any dialysis membrane that does not allow the polypeptide in the solution to pass therethrough can be used. An example of the dialysis membrane is a cellulose dialysis membrane. By repeating the substitution using the water-soluble solvent, the amount of the dissolving solvent can be reduced close to zero. In the latter half of the desolvation step, it is unnecessary to use a dialysis membrane. Thus, a polypeptide hydrogel having a moisture content of 85.0 to 99.9 mass % can be obtained. The polypeptide hydrogel having a moisture content in the above range is useful for artificial cartilage and artificial skin of a living body, a wound-healing agent, a medicament-encapsulated carrier in a drug delivery system, a buffer, etc.

The amount of the solvent, i.e., dimethyl sulfoxide (DMSO) or N,N-dimethylformamide (DMF), remaining in the polypeptide after the substitution step using the water-soluble solvent can be measured by a nuclear magnetic resonance spectrometer (NMR). A 1,2-dichloroethane-formic acid solution can be used as an internal standard.

EXAMPLES

Examples

Hereinafter, the present invention will be described in further detail by way of examples. Note that the present invention is not limited to the following examples. Water is used as the water-soluble solvent in the examples.

<Methods of Various Measurements>

(1) Measurement of Remaining Amount of Solvent

As an internal standard, a 1,2-dichloroethane-formic acid solution at a concentration of 3,100 ppm (0.00310 mg/ml) was prepared. 500 μl of a protein solution (obtained by dissolving 0.1 g of a polypeptide hydrogel in 10 ml of formic acid) and 500 μl of an internal standard solution were mixed. For H-NMR measurement, an acetonitrile deuterated solvent was added to the mixed solution in an amount approximately equivalent to that of the mixture solution so as to dilute the solution to about two times. Then, H-NMR measurement was performed (NMR model: JNM-ECX 100 manufactured by JOEL Ltd.). The H-NMR integrated intensity of 1,2-dichloroethane (internal standard sample) was compared with the H-NMR integrated intensity of DMSO. A calibration curve was formed by preparing a DMSO-formic acid solution at 3 ppm to 3000 ppm and following the above-mentioned protocol. By comparison with the calibration curve, the concentration of DMSO in the protein solution was calculated. A nuclear magnetic resonator (NMR) manufactured by JOEL Ltd. was used for the measurement of the concentration of DMSO.

(2) Viscosity

An EMS machine manufactured by Kyoto Electronics Manufacturing Co., Ltd. was used.

(3) Moisture Content

The mass of a hydrogel produced in accordance with the present technique: W1 and the mass of a dried body obtained by completely drying the hydrogel: W2 were measured, and the measured values were substituted in the following formula 1 to determine the moisture content.

$$\text{Moisture content} = [(W1-W2) \times 100]/W1 \quad \text{formula 1}$$

Example 1

1. Preparation of Polypeptide

<Gene Synthesis of ADF3Kai-A>

A partial amino acid sequence of ADF3, which is one of two principal dragline silk proteins of Araneus diadematus, was obtained from the NCBI web database (NCBI Accession No.: AAC47010, GI: 1263287), and an amino acid sequence (SEQ ID NO: 5) composed of a start codon, an His 10-tag and an HRV3C Protease (Human rhinovirus 3C Protease) recognition site was added to the N-terminal of the partial amino acid sequence of ADF3, so as to synthesize a gene encoding a polypeptide (ADF3Kai-A) composed of an amino acid sequence (SEQ ID NO: 1), i.e., the 1st residue to the 631st residue from the N-terminal of the resultant sequence. Consequently, a pUC57 vector to which a gene of ADF3Kai-A composed of a base sequence represented by SEQ ID NO: 6 had been introduced was obtained (having an Nde I site immediately upstream of the 5' terminal of the gene and an Xba I site immediately downstream of the 5' terminal thereof). Thereafter, the gene was subjected to a restriction enzyme treatment with Nde I and EcoR I, and recombined into a pET22b(+) expression vector. Thus, a pET22b(+) vector to which the gene of ADF3Kai-A had been introduced was obtained.

<Expression of Protein>

The obtained pET22b(+) expression vector containing the gene sequence of ADF3Kai-A was transformed into Escherichia coli Rosetta (DE3). The obtained single colony was incubated for 15 hours in 2 mL of an LB culture medium containing ampicillin. Thereafter, 1.4 ml of said culture solution was added to 140 mL of an LB culture medium containing ampicillin, and incubated to an $OD_{600}$ of 3.5 under the conditions of 37° C. and 200 rpm. Next, the culture solution with the $OD_{600}$ of 3.5 was added to 7 L of a 2xYT culture medium containing ampicillin, together with 140 mL of 50% glucose, and incubated further to the $OD_{600}$ of 4.0. Thereafter, isopropyl-β-thiogalactopyranoside (IPTG) was added to the obtained culture solution with the $OD_{600}$ of 4.0 so that the final concentration would be 0.5 mM, thereby inducing the expression of protein. After a lapse of two hours from the addition of IPTG, the culture solution was centrifuged and bacterial cells were collected. Protein solutions prepared from the culture solution before the addition of IPTG and the culture solution after the addition of IPTG were each electrophoresed in a polyacrylamide gel. Consequently, a target band size (about 56.1 kDa) was observed with the addition of IPTG, and the expression of the target protein (ADF3Kai-A) was confirmed.

Purification (1) About 50 g of bacteria cells of the Escherichia coli expressing the ADF3Kai-A protein and 300 ml of a buffer solution AI (20 mM Tris-HCl, pH 7.4) were placed in a centrifuge tube (1000 ml). After dispersing the bacteria cells with a mixer ("T18 basic ULTRA TURRAX" manufactured by IKA, level 2), the dispersion was centrifuged (11,000 g, 10 minutes, room temperature) with a centrifuge ("Model 7000" manufactured by Kubota Corporation), and a supernatant was discarded.

(2) To a precipitate (bacteria cells) obtained by the centrifugation, 300 ml of the buffer solution AI and 3 ml of 0.1 M PMSF (dissolved by isopropanol) were added. After dispersing the precipitate for 3 minutes with the above mixer (level 2) manufactured by IKA, the bacteria cells were disrupted repeatedly for three times using a high-pressure homogenizer ("Panda Plus 2000" manufactured by GEA Niro Soavi).

(3) To the disrupted bacterial cells, 300 mL of a buffer solution B (50 mM Tris-HCL, 100 mM NaCl, pH 7.0) containing 3 w/v % of SDS was added. After dispersing well the bacterial cells with the above mixer (level 2) manufactured by IKA, the dispersion was stirred for 60 minutes with a shaker (manufactured by TAITEC CORPORATION, 200 rpm, 37° C.). Thereafter, the stirred dispersion was centrifuged (11,000 g, 30 minutes, room temperature) with the above centrifuge manufactured by Kubota Corporation, and a supernatant was discarded, whereby SDS washing granules (precipitate) were obtained.

(4) The SDS washing granules were suspended in a DMSO solution containing 1M lithium chloride so that the concentration would be 100 mg/mL, and heat-treated for 1 hour at 80° C. Thereafter, the heated suspension was centrifuged (11,000 g, 30 minutes, room temperature) with the above centrifuge manufactured by Kubota Corporation, and a supernatant was collected.

(5) Ethanol in an amount three times greater than that of the collected supernatant was prepared. The collected supernatant was added to the ethanol, and left to stand for 1 hour at room temperature. Thereafter, the resultant was centrifuged (11,000 g, 30 minutes, room temperature) with the above centrifuge manufactured by Kubota Corporation to collect aggregated protein. Next, a process of washing aggregated protein using pure water and collecting aggregated protein by centrifugation was repeated three times, and thereafter water was removed by a freeze dryer to collect freeze-dried powder. The purification degree of the target protein ADF3Kai-A (about 56.1 kDa) in the obtained freeze-dried powder was checked by analyzing images of the results of polyacrylamide gel electrophoresis (CBB staining) of said protein powder using Totallab (Nonlinear Dynamics). As a result, the purification degree of ADF3Kai-A was about 85%.

2. Adjustment of Solution 0.8 g of spider silk protein powder (ADF3Kai-A) was added to 20 ml of DMSO (containing 1M LiCl), followed by dissolution at 80° C. for 30 minutes. Then, dusts and bubbles were removed from the solution. The viscosity of the solution was 30.8 cP (centipoises). The solution was placed a dialysis tube (Cellulose Tube 36/32 manufactured by Sanko Junyaku Co., Ltd. (presently EIDIA Co., Ltd)).

3. Substitution with Water

The dialysis tube was placed in a beaker filled with 3 L of pure water, left to stand for 3 hours, and water was renewed. This operation was repeated six times in total. Thus, the spider silk protein in the solution aggregated, and a hydrogel in which almost all of DMSO was substituted with water was produced.

Figure 1:
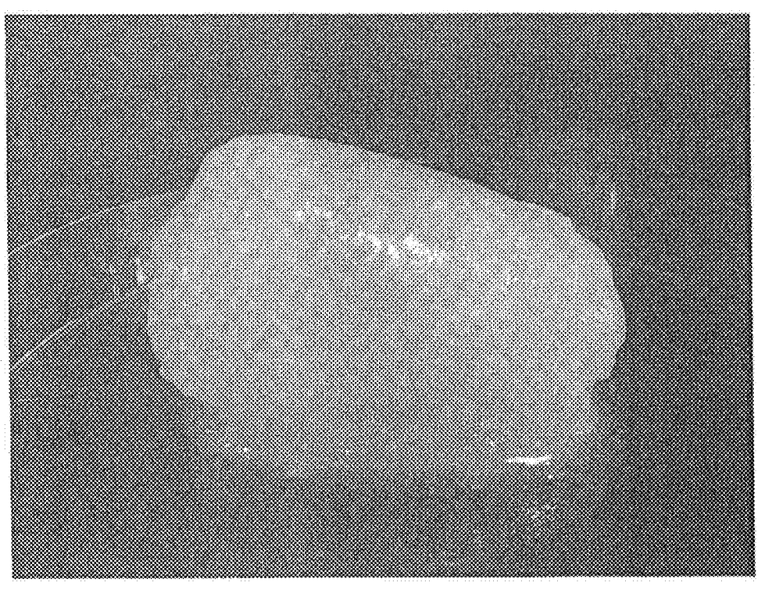
FIG. 1 is a photograph of a hydrogel in one example of the present invention.

4. Results (1) The amount of the solvent remaining in the obtained hydrogel was 0.094 g based on 100 g of the hydrogel.
(2) The moisture content of the obtained hydrogel was 95.3 mass %.
(3) FIG. 1 is a photograph showing the side of the obtained hydrogel.

Example 2

A gel of Example 2 was produced in the same manner as in Example 1 using the same polypeptide as that of Example 1. A 20 mg/ml dope (DMSO+1M LiCl) was prepared using 0.4 g of the polypeptide powder so as to produce a gel with a low concentration. The viscosity of the dope was 13.9 cP. The moisture content of the obtained gel was 98.8 mass %.

Example 3

A gel of Example 3 was produced in the same manner as in Example 1 using the same polypeptide as that of Example 1. A 20 mg/ml dope (DMSO without salt) was prepared using 0.4 g of the polypeptide powder so as to produce a gel. The moisture content of the obtained gel was 97.4 mass %.

Example 4

A gel of Example 4 was produced in the same manner as in Example 1 using the same polypeptide as that of Example 1. A 20 mg/ml dope (DMF+1M LiCl) was prepared using 0.4 g of the polypeptide powder so as to produce a gel. The moisture content of the obtained gel was 98.2 mass %.

Although water was used in the substitution step in the above Examples 1-4, the same effect can be obtained using other water-soluble solvents.

INDUSTRIAL APPLICABILITY

The hydrogel of the present invention is useful for cartilage for a living body, a buffer, and the like.

Sequence Listing Free Text
SEQ ID NOS: 1-5 amino acid sequences
SEQ ID NO: 6 base sequence

The invention claimed is:

1. A polypeptide hydrogel that is a hydrogel of a polypeptide derived from spider silk proteins, which has a moisture content of 85.0 to 99.9 mass % based on 100 mass % of the polypeptide hydrogel,
wherein at least one selected from the group consisting of dimethyl sulfoxide and N,N-dimethylformamide is present inside the polypeptide hydrogel.

2. A method for producing a polypeptide hydrogel, comprising:
a solution production step in which a polypeptide derived from spider silk proteins is dissolved in at least one dissolving solvent selected from the group consisting of: (A) dimethyl sulfoxide; (B) dimethyl sulfoxide with an inorganic salt; and (C) N,N-dimethylformamide with an inorganic salt, so as to obtain a solution of the polypeptide; and
a substitution step in which the solution of the polypeptide produced in the solution production step is substituted with a water-soluble solvent.

3. The method for producing a polypeptide hydrogel according to claim 2, wherein the substitution step is a step in which the solution of the polypeptide is substituted with water.

4. The method for producing a polypeptide hydrogel according to claim 2, wherein the substitution step is a step in which the solution of the polypeptide obtained by dissolving the polypeptide in the dissolving solvent is placed in a dialysis membrane, the dialysis membrane is immersed in a water-soluble solvent, and the water-soluble solvent is renewed at least one time.

5. The method for producing a polypeptide hydrogel according to claim 2, wherein the polypeptide hydrogel has a moisture content of 85.0 to 99.9 mass % based on 100 mass % of the polypeptide hydrogel.

* * * * *

SEQUENCE LISTING

```
<160> NUMBER OF SEQ ID NOS: 8

<210> SEQ ID NO 1
<211> LENGTH: 631
<212> TYPE: PRT
<213> ORGANISM: Artificial
<220> FEATURE:
<223> OTHER INFORMATION: ADF3Kai-A

<400> SEQUENCE: 1

Met His His His His His His His His His Ser Ser Gly Ser Ser
1               5                   10                  15

Leu Glu Val Leu Phe Gln Gly Pro Ala Arg Ala Gly Ser Gly Gln Gln
                20                  25                  30

Gly Pro Gly Gln Gln Gly Pro Gly Gln Gln Gly Pro Gly Gln Gln Gly
            35                  40                  45

Pro Tyr Gly Pro Gly Ala Ser Ala Ala Ala Ala Ala Ala Gly Gly Tyr
        50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
            115                 120                 125
```

-continued

```
Ala Gly Gly Asn Gly Pro Gly Ser Gly Gln Gln Gly Ala Gly Gln Gln
130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
                180                 185                 190

Ala Ala Gly Gly Tyr Gly Pro Gly Ser Gly Gln Gly Pro Gly Gln Gln
            195                 200                 205

Gly Pro Gly Gly Gln Gly Pro Tyr Gly Pro Gly Ala Ser Ala Ala Ala
210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
                245                 250                 255

Pro Gly Ala Ser Ala Ala Ala Ala Ala Gly Gly Tyr Gly Pro Gly
                260                 265                 270

Tyr Gly Gln Gln Gly Pro Gly Gln Gln Gly Pro Gly Gly Gln Gly Pro
    275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Ala Gly Gly
                325                 330                 335

Tyr Gly Pro Gly Ser Gly Gln Gln Gly Pro Gly Gln Gln Gly Pro Gly
                340                 345                 350

Gln Gln Gly Pro Gly Gln Gln Gly Pro Gly Gln Gln Gly Pro Tyr Gly
                355                 360                 365

Pro Gly Ala Ser Ala Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
                420                 425                 430

Gln Gly Ala Tyr Gly Pro Gly Ala Ser Ala Ala Gly Ala Ala Gly
            435                 440                 445

Gly Tyr Gly Pro Gly Ser Gly Gln Gln Gly Pro Gly Gln Gln Gly Pro
    450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Gly Gly Tyr Gly Pro Gly
                500                 505                 510

Ser Gly Gln Gln Gly Pro Gly Gln Gln Gly Pro Gly Gln Gln Gly Pro
515                 520                 525

Gly Gly Gln Gly Pro Tyr Gly Pro Gly Ala Ala Ser Ala Ala Val Ser
530                 535                 540
```

Val Gly Gly Tyr Gly Pro Gln Ser Ser Val Pro Val Ala Ser Ala
545                 550                 555                 560

Val Ala Ser Arg Leu Ser Ser Pro Ala Ala Ser Ser Arg Val Ser Ser
            565                 570                 575

Ala Val Ser Ser Leu Val Ser Ser Gly Pro Thr Lys His Ala Ala Leu
        580                 585                 590

Ser Asn Thr Ile Ser Ser Val Val Ser Gln Val Ser Ala Ser Asn Pro
            595                 600                 605

Gly Leu Ser Gly Cys Asp Val Leu Val Gln Ala Leu Leu Glu Val Val
        610                 615                 620

Ser Ala Leu Val Ser Ile Leu
625                 630

<210> SEQ ID NO 2
<211> LENGTH: 1154
<212> TYPE: PRT
<213> ORGANISM: Artificial
<220> FEATURE:
<223> OTHER INFORMATION: ADF3Kai-Large-NRSH1

<400> SEQUENCE: 2

Met His His His His His His His His Ser Ser Gly Ser Ser
1               5                   10                  15

Leu Glu Val Leu Phe Gln Gly Pro Ala Arg Ala Gly Ser Gly Gln Gln
                20                  25                  30

Gly Pro Gly Gln Gln Gly Pro Gly Gln Gln Gly Pro Gly Gln Gln Gly
            35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
        115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gln Gly Pro Tyr Gly
                245                 250                 255

Pro Gly Ala Ser Ala Ala Ala Ala Ala Ala Gly Gly Tyr Gly Pro Gly
            260                 265                 270

-continued

```
Tyr Gly Gln Gly Pro Gln Gly Pro Gly Gln Gly Pro
            275             280             285
Tyr Gly Pro Gly Ala Ser Ala Ala Ser Ala Ala Ser Gly Gly Tyr Gly
            290             295             300
Pro Gly Ser Gly Gln Gln Gly Pro Gly Gln Gly Pro Gly Gln
305             310             315             320
Gly Pro Tyr Gly Pro Gly Ala Ser Ala Ala Ala Ala Gly Gly
            325             330             335
Tyr Gly Pro Gly Ser Gly Gln Gln Gly Pro Gly Gln Gly Pro Gly
            340             345             350
Gln Gln Gly Pro Gly Gln Gln Gly Pro Gly Gln Gly Pro Tyr Gly
            355             360             365
Pro Gly Ala Ser Ala Ala Ala Ala Ala Gly Gly Tyr Gly Pro Gly
            370             375             380
Ser Gly Gln Gln Gly Pro Gly Gln Gln Gly Pro Gly Gln Gln Gly Pro
385             390             395             400
Gly Gln Gln Gly Pro Gly Gln Gln Gly Pro Gly Gln Gln Gly Pro Gly
            405             410             415
Gln Gln Gly Pro Gly Gln Gln Gly Pro Gly Gln Gln Gly Pro Gly Gly
            420             425             430
Gln Gly Ala Tyr Gly Pro Gly Ala Ser Ala Ala Ala Gly Ala Ala Gly
            435             440             445
Gly Tyr Gly Pro Gly Ser Gly Gln Gln Gly Pro Gly Gln Gln Gly Pro
            450             455             460
Gly Gln Gln Gly Pro Gly Gln Gln Gly Pro Gly Gln Gln Gly Pro Gly
465             470             475             480
Gln Gln Gly Pro Gly Gln Gln Gly Pro Gly Gln Gln Gly Pro Tyr Gly
            485             490             495
Pro Gly Ala Ser Ala Ala Ala Ala Ala Gly Gly Tyr Gly Pro Gly
            500             505             510
Ser Gly Gln Gln Gly Pro Gly Gln Gln Gly Pro Gly Gln Gln Gly Pro
            515             520             525
Gly Gly Gln Gly Pro Tyr Gly Pro Gly Ala Ala Ser Ala Ala Val Ser
            530             535             540
Val Ser Arg Ala Arg Ala Gly Ser Gly Gln Gln Gly Pro Gly Gln Gln
545             550             555             560
Gly Pro Gly Gln Gln Gly Pro Gly Gln Gln Gly Pro Tyr Gly Pro Gly
            565             570             575
Ala Ser Ala Ala Ala Ala Ala Gly Gly Tyr Gly Pro Gly Ser Gly
            580             585             590
Gln Gln Gly Pro Ser Gln Gln Gly Pro Gly Gln Gln Gly Pro Gly Gly
            595             600             605
Gln Gly Pro Tyr Gly Pro Gly Ala Ser Ala Ala Ala Ala Ala Gly
            610             615             620
Gly Tyr Gly Pro Gly Ser Gly Gln Gln Gly Pro Gly Gln Gln Gly Pro
625             630             635             640
Tyr Gly Pro Gly Ser Ser Ala Ala Ala Ala Ala Gly Gly Asn Gly
            645             650             655
Pro Gly Ser Gly Gln Gln Gly Ala Gly Gln Gln Gly Pro Gly Gln Gln
            660             665             670
Gly Pro Gly Ala Ser Ala Ala Ala Ala Ala Gly Gly Tyr Gly Pro
            675             680             685
```

-continued

```
Gly Ser Gly Gln Gln Gly Pro Gly Gln Gln Gly Pro Gly Gln Gly
    690                 695                 700
Pro Tyr Gly Pro Gly Ala Ser Ala Ala Ala Ala Ala Gly Gly Tyr
    705                 710                 715                 720
Gly Pro Gly Ser Gly Gln Gly Pro Gly Gln Gln Gly Pro Gly Gln
                    725                 730                 735
Gly Pro Tyr Gly Pro Gly Ala Ser Ala Ala Ala Ala Ala Gly Gly
                740                 745                 750
Tyr Gly Pro Gly Ser Gly Gln Gly Pro Gly Gln Gln Gly Pro Gly
            755                 760                 765
Gln Gln Gly Pro Gly Gly Gln Gly Pro Tyr Gly Pro Gly Ala Ser Ala
    770                 775                 780
Ala Ala Ala Ala Ala Gly Gly Tyr Gly Pro Gly Tyr Gly Gln Gln Gly
    785                 790                 795                 800
Pro Gly Gln Gln Gly Pro Gly Gly Gln Gly Pro Tyr Gly Pro Gly Ala
                    805                 810                 815
Ser Ala Ala Ser Ala Ala Ser Gly Gly Tyr Gly Pro Gly Ser Gly Gln
                820                 825                 830
Gln Gly Pro Gly Gln Gln Gly Pro Gly Gly Gln Gly Pro Tyr Gly Pro
            835                 840                 845
Gly Ala Ser Ala Ala Ala Ala Ala Gly Gly Tyr Gly Pro Gly Ser
    850                 855                 860
Gly Gln Gln Gly Pro Gly Gln Gln Gly Pro Gly Gln Gln Gly Pro Gly
865                 870                 875                 880
Gln Gln Gly Pro Gly Gly Gln Gly Pro Tyr Gly Pro Gly Ala Ser Ala
                    885                 890                 895
Ala Ala Ala Ala Gly Gly Tyr Gly Pro Gly Ser Gly Gln Gln Gly
                900                 905                 910
Pro Gly Gln Gln Gly Pro Gly Gln Gln Gly Pro Gly Gln Gln Gly Pro
    915                 920                 925
Gly Gln Gln Gly Pro Gly Gln Gln Gly Pro Gly Gln Gln Gly Pro Gly
    930                 935                 940
Gln Gln Gly Pro Gly Gln Gln Gly Pro Gly Gly Gln Gly Ala Tyr Gly
945                 950                 955                 960
Pro Gly Ala Ser Ala Ala Gly Ala Ala Gly Gly Tyr Gly Pro Gly
                965                 970                 975
Ser Gly Gln Gln Gly Pro Gly Gln Gln Gly Pro Gly Gln Gln Gly Pro
                980                 985                 990
Gly Gln Gln Gly Pro Gly Gln Gln Gly Pro Gly Gln Gln Gly Pro Gly
            995                 1000                1005
Gln Gln Gly Pro Gly Gln Gln Gly Pro Tyr Gly Pro Gly Ala Ser
    1010                1015                1020
Ala Ala Ala Ala Ala Ala Gly Gly Tyr Gly Pro Gly Ser Gly Gln
    1025                1030                1035
Gln Gly Pro Gly Gln Gln Gly Pro Gly Gln Gln Gly Pro Gly Gly
    1040                1045                1050
Gln Gly Pro Tyr Gly Pro Gly Ala Ala Ser Ala Ala Val Ser Val
    1055                1060                1065
Gly Gly Tyr Gly Pro Gln Ser Ser Val Pro Val Ala Ser Ala
    1070                1075                1080
Val Ala Ser Arg Leu Ser Ser Pro Ala Ala Ser Ser Arg Val Ser
    1085                1090                1095
```

```
Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu
    1145                1150

<210> SEQ ID NO 3
<211> LENGTH: 660
<212> TYPE: PRT
<213> ORGANISM: Artificial
<220> FEATURE:
<223> OTHER INFORMATION: ADF3Kai

<400> SEQUENCE: 3

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
        115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
                245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
        275                 280                 285

Tyr Gly Pro Gly Ala Ser Ala Ala Ser Ala Ala Ser Gly Gly Tyr Gly
    290                 295                 300
```

```
Pro Gly Ser Gly Gln Gln Gly Pro Gly Gln Gln Gly Pro Gly Gly Gln
305                 310                 315                 320
Gly Pro Tyr Gly Pro Gly Ala Ser Ala Ala Ala Ala Ala Ala Gly Gly
            325                 330                 335
Tyr Gly Pro Gly Ser Gly Gln Gln Gly Pro Gly Gln Gln Gly Pro Gly
        340                 345                 350
Gln Gln Gly Pro Gly Gln Gln Gly Pro Gly Gln Gln Gly Pro Tyr Gly
    355                 360                 365
Pro Gly Ala Ser Ala Ala Ala Ala Ala Ala Gly Tyr Gly Pro Gly
370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
            405                 410                 415
Gln Gln Gly Pro Gly Gln Gln Gly Pro Gly Gln Gln Gly Pro Gly Gly
            420                 425                 430
Gln Gly Ala Tyr Gly Pro Gly Ala Ser Ala Ala Gly Ala Ala Gly
        435                 440                 445
Gly Tyr Gly Pro Gly Ser Gly Gln Gln Gly Pro Gly Gln Gln Gly Pro
    450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
            485                 490                 495
Pro Gly Ala Ser Ala Ala Ala Ala Ala Gly Gly Tyr Gly Pro Gly
        500                 505                 510
Ser Gly Gln Gln Gly Pro Gly Gln Gln Gly Pro Gly Gln Gln Gly Pro
    515                 520                 525
Gly Gly Gln Gly Pro Tyr Gly Pro Gly Ala Ala Ser Ala Ala Val Ser
530                 535                 540
Val Gly Gly Tyr Gly Pro Gln Ser Ser Val Pro Val Ala Ser Ala
545                 550                 555                 560
Val Ala Ser Arg Leu Ser Ser Pro Ala Ala Ser Arg Val Ser Ser
            565                 570                 575
Ala Val Ser Ser Leu Val Ser Ser Gly Pro Thr Lys His Ala Ala Leu
        580                 585                 590
Ser Asn Thr Ile Ser Ser Val Val Ser Gln Val Ser Ala Ser Asn Pro
    595                 600                 605
Gly Leu Ser Gly Cys Asp Val Leu Val Gln Ala Leu Leu Glu Val Val
610                 615                 620
Ser Ala Leu Val Ser Ile Leu Gly Ser Ser Ile Gly Gln Ile Asn
625                 630                 635                 640
Tyr Gly Ala Ser Ala Gln Tyr Thr Gln Met Val Gly Gln Ser Val Ala
            645                 650                 655
Gln Ala Leu Ala
        660

<210> SEQ ID NO 4
<211> LENGTH: 1183
<212> TYPE: PRT
<213> ORGANISM: Artificial
<220> FEATURE:
<223> OTHER INFORMATION: ADF3Kai-Large
```

<400> SEQUENCE: 4

```
Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gln Gln Gly Pro Gln Gln Gly
            35                  40                  45

Pro Tyr Gly Pro Gly Ala Ser Ala Ala Ala Ala Ala Gly Gly Tyr
        50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
            115                 120                 125

Ala Gly Gly Asn Gly Pro Gly Ser Gly Gln Gln Gly Ala Gly Gln Gln
        130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gln Gly Pro Tyr Gly Pro Gly Ala Ser Ala Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gln Gly Pro Tyr Gly
                245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gln Gly Pro
            275                 280                 285

Tyr Gly Pro Gly Ala Ser Ala Ala Ser Ala Ala Ser Gly Gly Tyr Gly
        290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Ala Gly Gly
                325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gly Gln Gly Pro Tyr Gly
        355                 360                 365

Pro Gly Ala Ser Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415
```

```
Gln Gln Gly Pro Gly Gln Gln Gly Pro Gly Gln Gln Gly Gly
            420                 425                 430

Gln Gly Ala Tyr Gly Pro Gly Ala Ser Ala Ala Gly Ala Ala Gly
            435                 440                 445

Gly Tyr Gly Pro Gly Ser Gly Gln Gln Gly Pro Gly Gln Gln Gly Pro
            450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
            485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
            515                 520                 525

Gly Gly Gln Gly Pro Tyr Gly Pro Gly Ala Ala Ser Ala Ala Val Ser
            530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
            565                 570                 575

Ala Ser Ala Ala Ala Ala Ala Ala Gly Gly Tyr Gly Pro Gly Ser Gly
            580                 585                 590

Gln Gln Gly Pro Ser Gln Gln Gly Pro Gly Gln Gln Gly Pro Gly Gly
            595                 600                 605

Gln Gly Pro Tyr Gly Pro Gly Ala Ser Ala Ala Ala Ala Ala Gly
            610                 615                 620

Gly Tyr Gly Pro Gly Ser Gly Gln Gln Gly Pro Gly Gly Gln Gly Pro
625                 630                 635                 640

Tyr Gly Pro Gly Ser Ser Ala Ala Ala Ala Ala Gly Gly Asn Gly
            645                 650                 655

Pro Gly Ser Gly Gln Gln Gly Ala Gly Gln Gln Gly Pro Gly Gln Gln
            660                 665                 670

Gly Pro Gly Ala Ser Ala Ala Ala Ala Ala Gly Gly Tyr Gly Pro
            675                 680                 685

Gly Ser Gly Gln Gln Gly Pro Gly Gln Gln Gly Pro Gly Gly Gln Gly
            690                 695                 700

Pro Tyr Gly Pro Gly Ala Ser Ala Ala Ala Ala Ala Gly Gly Tyr
705                 710                 715                 720

Gly Pro Gly Ser Gly Gln Gln Gly Pro Gly Gln Gln Gly Pro Gly Gln
            725                 730                 735

Gly Pro Tyr Gly Pro Gly Ala Ser Ala Ala Ala Ala Ala Gly Gly
            740                 745                 750

Tyr Gly Pro Gly Ser Gln Gln Gly Pro Gly Gln Gln Gly Pro Gly
            755                 760                 765

Gln Gln Gly Pro Gly Gly Gln Gly Pro Tyr Gly Pro Gly Ala Ser Ala
            770                 775                 780

Ala Ala Ala Ala Gly Gly Tyr Gly Pro Gly Tyr Gly Gln Gln Gly
785                 790                 795                 800

Pro Gly Gln Gln Gly Pro Gly Gly Gln Gly Pro Tyr Gly Pro Gly Ala
            805                 810                 815
```

```
Ser Ala Ala Ser Ala Ala Ser Gly Gly Tyr Gly Pro Gly Ser Gly Gln
                820                 825                 830

Gln Gly Pro Gly Gln Gln Gly Pro Gly Gln Gly Pro Tyr Gly Pro
        835                 840                 845

Gly Ala Ser Ala Ala Ala Ala Ala Gly Gly Tyr Gly Pro Gly Ser
    850                 855                 860

Gly Gln Gln Gly Pro Gly Gln Gln Gly Pro Gly Gln Gln Gly Pro Gly
865                 870                 875                 880

Gln Gln Gly Pro Gly Gln Gly Pro Tyr Gly Pro Gly Ala Ser Ala
                885                 890                 895

Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
        915                 920                 925

Gly Gln Gln Gly Pro Gly Gln Gln Gly Pro Gly Gln Gln Gly Pro Gly
    930                 935                 940

Gln Gln Gly Pro Gly Gln Gln Gly Pro Gly Gln Gly Ala Tyr Gly
945                 950                 955                 960

Pro Gly Ala Ser Ala Ala Ala Gly Ala Ala Gly Gly Tyr Gly Pro Gly
                965                 970                 975

Ser Gly Gln Gln Gly Pro Gly Gln Gln Gly Pro Gly Gln Gln Gly Pro
        980                 985                 990

Gly Gln Gln Gly Pro Gly Gln Gln  Gly Pro Gly Gln Gln  Gly Pro Gly
    995                 1000                1005

Gln Gln  Gly Pro Gly Gln Gln  Gly Pro Tyr Gly Pro  Gly Ala Ser
    1010                1015                1020

Ala Ala  Ala Ala Ala Ala Gly  Gly Tyr Gly Pro Gly  Ser Gly Gln
    1025                1030                1035

Gln Gly  Pro Gly Gln Gln Gly  Pro Gly Gln Gln Gly  Pro Gly Gly
    1040                1045                1050

Gln Gly  Pro Tyr Gly Pro Gly  Ala Ala Ser Ala Ala  Val Ser Val
    1055                1060                1065

Gly Gly  Tyr Gly Pro Gln Ser  Ser Ser Val Pro Val  Ala Ser Ala
    1070                1075                1080

Val Ala  Ser Arg Leu Ser Ser  Pro Ala Ala Ser Ser  Arg Val Ser
    1085                1090                1095

Ser Ala  Val Ser Ser Leu Val  Ser Ser Gly Pro Thr  Lys His Ala
    1100                1105                1110

Ala Leu  Ser Asn Thr Ile Ser  Ser Val Val Ser Gln  Val Ser Ala
    1115                1120                1125

Ser Asn  Pro Gly Leu Ser Gly  Cys Asp Val Leu Val  Gln Ala Leu
    1130                1135                1140

Leu Glu  Val Val Ser Ala Leu  Val Ser Ile Leu Gly  Ser Ser Ser
    1145                1150                1155

Ile Gly  Gln Ile Asn Tyr Gly  Ala Ser Ala Gln Tyr  Thr Gln Met
    1160                1165                1170

Val Gly  Gln Ser Val Ala Gln  Ala Leu Ala
    1175                1180

<210> SEQ ID NO 5
<211> LENGTH: 24
<212> TYPE: PRT
<213> ORGANISM: Artificial
<220> FEATURE:
<223> OTHER INFORMATION: His tag and start codon
```

<400> SEQUENCE: 5

Met His His His His His His His His His Ser Ser Gly Ser Ser
1               5                   10                  15

Leu Glu Val Leu Phe Gln Gly Pro
            20

<210> SEQ ID NO 6
<211> LENGTH: 1983
<212> TYPE: DNA
<213> ORGANISM: Artificial
<220> FEATURE:
<223> OTHER INFORMATION: ADF3Kai-A

<400> SEQUENCE: 6

| | | | | |
|---|---|---|---|---|
| atgcatcacc | atcatcatca | tcaccaccac | cattcctcgg | gctcatcctt | ggaagtgtta | 60 |
| tttcaaggac | agcacgagc | cggttcggga | caacaagggc | ctggccagca | gggcccaggt | 120 |
| caacaagggc | caggacagca | gggtccttat | gggcccggcg | caagcgcagc | agctgcggcc | 180 |
| gctggtggct | atggtcctgg | ctccggtcaa | cagggcccct | cgcaacaagg | tcccgggcag | 240 |
| caaggtcctg | gtggccaggg | tccctacggg | ccggggggcga | gtgcggcagc | agccgctgca | 300 |
| ggcggttatg | gtccaggaag | cggacagcaa | ggtccggag | gtcaaggtcc | gtatggccca | 360 |
| ggctctagcg | cggctgccgc | tgccgcgggt | ggcaacggac | agggagcgg | acaacagggc | 420 |
| gcgggacaac | agggtccagg | acagcaaggc | caggggcgt | cggcggctgc | agcggcggcc | 480 |
| ggaggctatg | acccggctc | aggacaacag | ggaccgggtc | aacaaggacc | cggtggccaa | 540 |
| ggcccctatg | cccggggcgc | cagcgcggcc | gcagccgccg | cggggcgggta | cggcccggt | 600 |
| agcggccagg | gaccaggtca | gcaggggcca | ggaggtcagg | gcccatacgg | tccgggcgca | 660 |
| tccgcggcgg | cggcagcggc | aggtggctac | ggtcccggaa | gcggccaaca | ggggccaggg | 720 |
| caacaaggac | caggacaaca | aggtcctggg | ggccaaggac | cgtatggacc | aggagcatca | 780 |
| gctgcagccg | cggcagctgg | cggttacggt | ccaggctacg | gccagcaggg | tccgggtcag | 840 |
| cagggaccgg | gaggccaggg | gccttatggc | cctggcgctt | ccgcagccag | tgccgcttct | 900 |
| ggaggatacg | gccgggaag | cggtcagcaa | ggccctggcc | aacaaggacc | tggaggccaa | 960 |
| gggccctacg | gcccaggagc | tcggcagcc | gcagctgccg | caggtgggta | tgggccaggt | 1020 |
| agcgggcaac | aagggccggg | tcagcaagga | ccggggcaac | agggacctgg | gcagcaagga | 1080 |
| cccgggggtc | aaggcccgta | cggacctggt | gcgtctgcag | ctgctgctgc | ggctggtgga | 1140 |
| tatggtccgg | gatcggggca | gcagggtccc | ggtcagcagg | gcctggtca | gcaagggcca | 1200 |
| ggccaacagg | gaccggaca | caaggcccg | ggtcaacagg | gtcctggaca | gcaggggccg | 1260 |
| ggccaacaag | gccctgggca | acaggtccg | ggggacagg | gggcctatgg | gcctggcgca | 1320 |
| tctgccgccg | ctggcgcagc | cggtgggtac | gggcctgggt | caggtcaaca | ggggcctggt | 1380 |
| caacaaggcc | ccgggcaaca | gggccccggc | cagcaaggtc | cagggcagca | gggcccggga | 1440 |
| cagcaagggc | ctggacaaca | gggccccgga | cagcaggac | cttacggccc | cggtgcgagc | 1500 |
| gcagcggccg | ccgccgcagg | gggatatggc | cccggatcgg | gccagcaggg | accaggccag | 1560 |
| caaggacctg | gccaacaggg | cccgggggt | caggggccgt | atggtcccgg | cgctgcaagt | 1620 |
| gctgcagtgt | ccgttggagg | ttacggccct | cagtcttcgt | ctgttccggt | ggcgtccgca | 1680 |
| gttgcgagta | gactgtcttc | acctgctgct | tcatcgcgag | tatcgagcgc | tgtttcgtct | 1740 |
| cttgtctcgt | cgggtcccac | gaaacatgcc | gcccttttcaa | atacgatttc | atctgtagtg | 1800 |
| tcccaagtta | gtgcaagtaa | cccgggggtta | tccgatgcg | acgttctcgt | tcaggcactc | 1860 |

-continued

```
ctagaagtag tatccgcgtt ggtgagcatc ttataaagct cctcgatagg tcaaataaac    1920
tatggtgctt cagcccagta tacacagatg gtgggacaga gcgtcgcgca ggcattggct    1980
taa                                                                 1983
```

```
<210> SEQ ID NO 7
<211> LENGTH: 26
<212> TYPE: PRT
<213> ORGANISM: Artificial
<220> FEATURE:
<223> OTHER INFORMATION: Formula 2
<220> FEATURE:
<221> NAME/KEY: UNSURE
<222> LOCATION: (3)..(12)
<223> OTHER INFORMATION: Xaa at position 3 is any one of amino acids,
      preferably is Ala, Tyr or Gln; Xaa at positions 4-6,7-9,10-12 is
      present or absent, when present, Xaa at positions 4-5,7-8,10-11 is
      Gly and Xaa at positions 6,9,12 is any one of amino acids
      preferably is Ala, Tyr or Gln.
<220> FEATURE:
<221> NAME/KEY: UNSURE
<222> LOCATION: (13)..(20)
<223> OTHER INFORMATION: Xaa at positions 13-14, 15-16, 17-18, 19-20 is
      present or absent, when present, Xaa at positions 13, 15, 17, 19
      is Gly and Xaa at positions 14, 16, 18, 20 is Ala.
<220> FEATURE:
<221> NAME/KEY: UNSURE
<222> LOCATION: (22)..(26)
<223> OTHER INFORMATION: Xaa at positions 22-26 is present or absent,
      when present is Ala.

<400> SEQUENCE: 7

Gly Gly Xaa Xaa Xaa Xaa Xaa Xaa Xaa Xaa Xaa Xaa Xaa Xaa Xaa Xaa
1               5                   10                  15

Xaa Xaa Xaa Xaa Ala Xaa Xaa Xaa Xaa Xaa
            20                  25

<210> SEQ ID NO 8
<211> LENGTH: 5
<212> TYPE: PRT
<213> ORGANISM: Artificial
<220> FEATURE:
<223> OTHER INFORMATION: Formula 3
<220> FEATURE:
<221> NAME/KEY: UNSURE
<222> LOCATION: (1)..(5)
<223> OTHER INFORMATION: Xaa at position 5 is any one of amino acids, in
      particular, it preferably is Ala, Ser, Tyr or Val.

<400> SEQUENCE: 8

Gly Pro Gly Gly Xaa
1               5
```